US006355275B1

(12) United States Patent
Klein

(10) Patent No.: US 6,355,275 B1
(45) Date of Patent: Mar. 12, 2002

(54) EMBOLIZATION USING CARBON COATED MICROPARTICLES

(75) Inventor: Dean A. Klein, North Oaks, MN (US)

(73) Assignee: Carbon Medical Technologies, Inc., St. Paul, MN (US)

( * ) Notice: Subject to any disclaimer, the term of this patent is extended or adjusted under 35 U.S.C. 154(b) by 0 days.

(21) Appl. No.: 09/602,323

(22) Filed: Jun. 23, 2000

(51) Int. Cl.$^7$ .................... A61P 7/04; A61K 49/04; A61K 9/16; A61K 3/08; A61L 31/02

(52) U.S. Cl. ................. 424/490; 424/9.3; 424/9.4; 424/9.42; 424/423; 424/688; 424/691

(58) Field of Search .................. 424/9.4, 9.5, 9.6, 424/9.3, 423, 688, 691, 649, 490, 9.42; 514/834

(56) References Cited

U.S. PATENT DOCUMENTS

| 3,334,050 A | 8/1967 | Grotenhuis et al. ...... 252/301.1 |
| 3,746,650 A | 7/1973 | Lahr et al. ............. 252/301.1 |
| 4,341,220 A | 7/1982 | Perry ..................... 128/630 |
| 4,627,853 A | 12/1986 | Campbell et al. ........... 623/16 |
| 4,709,703 A | 12/1987 | Lazarow et al. ............ 424/1.1 |
| 4,795,463 A | 1/1989 | Gerow ...................... 623/8 |
| 4,997,454 A | 3/1991 | Violante et al. ............ 23/305 |
| 4,999,188 A | 3/1991 | Solodovnik et al. |
| 5,108,399 A | 4/1992 | Eitenmuller et al. ......... 606/77 |
| 5,202,352 A | 4/1993 | Okada et al. .............. 514/475 |
| 5,236,410 A | 8/1993 | Granov et al. ............. 600/12 |
| 5,366,507 A | 11/1994 | Scottosanti .................. 623/16 |
| 5,382,260 A | 1/1995 | Dormandy, Jr. et al. .... 606/151 |
| 5,441,517 A | 8/1995 | Kensey et al. ............. 606/213 |
| 5,451,406 A | 9/1995 | Lawin et al. .............. 424/423 |
| 5,476,472 A | 12/1995 | Dormandy, Jr. et al. .... 606/151 |
| 5,624,685 A | 4/1997 | Takahashi et al. .......... 424/488 |
| 5,635,215 A | 6/1997 | Boschetti et al. ........... 424/501 |
| 5,648,100 A | 7/1997 | Boschetti et al. ........... 424/501 |
| 5,665,092 A | 9/1997 | Mangiardi et al. ........... 606/86 |
| 5,676,146 A | 10/1997 | Scarborough .............. 128/654 |
| 5,702,361 A | 12/1997 | Evans et al. ............... 604/53 |
| 5,746,734 A | 5/1998 | Dormandy, Jr. et al. ........ 606/1 |
| 5,792,478 A | 8/1998 | Lawin et al. .............. 424/502 |
| 5,830,230 A | 11/1998 | Berryman et al. .......... 606/200 |
| 5,891,058 A | 4/1999 | Taki et al. ................ 600/585 |
| 5,894,022 A | 4/1999 | Ji et al. .................. 424/422 |
| 5,902,310 A | 5/1999 | Foerster et al. ............ 606/142 |
| 5,941,890 A | 8/1999 | Voegele et al. ............ 606/151 |
| RE36,461 E | 12/1999 | Russell et al. ............. 604/180 |
| 6,015,424 A | 1/2000 | Rosenbluth et al. ........ 606/200 |
| 6,017,977 A | 1/2000 | Evans et al. ............... 523/113 |
| 6,056,700 A | 5/2000 | Burney et al. ............. 600/564 |
| 6,086,544 A | 7/2000 | Hibner et al. ............. 600/568 |
| 6,161,034 A | 12/2000 | Burbank et al. ............ 600/431 |

FOREIGN PATENT DOCUMENTS

| WO | WO 94/21196 | 9/1994 |
| WO | WO 99/12577 | 3/1999 |
| WO | WO 99/43366 | 9/1999 |
| WO | WO 99/43380 | 9/1999 |
| WO | WO 99/44643 | 9/1999 |
| WO | WO 01/00101 | 1/2001 |

OTHER PUBLICATIONS

Beavan, Al., "Material Properties and Applications of Pyrolite® Carbon", as published in Materials Engineering, Feb. 1990, pp 1–5.

Malizia, Anthony A., Jr., Reiman, Herbert M., Meyers, Robert P., Sande, Jonathan R., Barham, Steven S., Benson, Ralph C., Jr., Dewanjee, Mrinal K., and Utz, William J., "Migration and Granulomatous Reaction After Periurethral Injection of Polytef (Teflon)," JAMA, Jun. 22/29, 1984 vol. 251, No. 24.

Goldberg, Ronald P., MD, Hall, Ferris M., M.D., and Simon, Morris, MD. "Preoperative Localization of Non–Palpable Breast Lesions Using a Wire Marker and Perforated Mammographic Grid," Radiology 146: 833–835, Mar. 1983.

Fajardo, Laurie L., MD, Bird, Richard E., MD, Herman, Cheryl R., MD, DeAngalis, Gia A., MD, "Placement of Endovascular Embolization Microcoils to Localize the Site of Breast Lesions Removal at Sterotactic Core Biopsy," Radiology, 1998, 206: 275–278.

Liberman, Laura, MD, Dershaw, David, MD, Morris, Elizabeth A., MD, Abramson, Andrea F., MD, Thorton, Cynthia M., RT (R)(M), Rosen Paul Peter, MD, "Clip Placement After Stereotactic Vacuum–Assisted Breast Biopsy," Radiology, 1997; 205:417–422.

Burbank, Fred, MD, Farcier, Nancy, MD, "Tissue Marking Clip for Stereotactic Breast Biopsy: Initial Placement Accuracy, Long–term Stability, and Usefulness as a Guide for Wire Localization," Radiology 1997; 205:407–415.

Jonathan I., Epstein MD, "Are You Getting The Maximum Diagnostic and Prognostic Information from your Prostate Needle Biopsy?" Contemporary Urology, Apr. 1999, pp. 106–118.

Berman, MF., Hartmann A., Mast H., Sciacca RR., Mohr JP., Pile–Spellman J., Young WL., "eterminants of Resource Utilization in the Treatment of Brain Arteriovenous Malformations," Ajnr: American Journal of Neuroradiology, 20(10):2004–8, Nov.–Dec. 1999.

Abel, G., and Czop, J.K., "Stimulation of Human Monocyte B–glucan Receptors by Glucan Particles Induces Production of TNF–∂ and 1L–B," *Int. J. Immunopharmacol.*, 14(8):1363–1373, 1992.

(List continued on next page.)

*Primary Examiner*—Edward J. Webman
*Assistant Examiner*—Helen Nguyen
(74) *Attorney, Agent, or Firm*—Faegre & Benson LLP

(57) ABSTRACT

Described are methods of embolization using an embolizing agent composition that includes microparticles with carbon surfaces, and comprising a contrast agent. Preferred microparticles include a permanently radiopaque particle substrate and a pyrolytic carbon surface.

28 Claims, No Drawings

OTHER PUBLICATIONS

Nagino M., Kamiya J., Kanai M., Uesaka K., Sano T., Yamamoto H., Hayakawa N., Nimura Y., "Right Trisegment Portal Vein Embolization for Biliary Tract Carcinoma: Technique and Clinical Utility," Surgery, 127(2):155–60, Feb. 2000.

(Abstract) Kalman D. Varenhorst E., "The Role of Arterial Embolization in Renal Cell Carcinoma," Scandinavian Journal of Urology & Nephrology, 33(3):162–70, Jun. 1999.

(Abstract) Lee W., Kim TS., Chung JW., Han JK., Kim SH., Park JH., "Renal Angiomyolipoma: Embolotherapy with a Mixture of Alcohol and Iodized Oil," Journal of Vascular & Interventional Radiology, 9(2):255–61, Mar.–Apr. 1998.

(Abstract) Layelle I., Flandroy P., Trotteur G., Dondelinger RF., "Arterial Embolization of Bone Metastases: is it Worthwhile?" Journal Belge de Radiologie, 81(5):223–5, Oct. 1998.

(Abstract) Mourikis D., Chatziioannou A., Antoniou A., Kehagias D., Gikas D., Vlahos L., "Selective Arterial Embolization in the Management of Symptomatic Renal Angiomyolipomas", European Journal of Radioloby, 32(3): 153–9, Dec. 1999.

Malizia, Jr. MD, Anthony A.; Reiman, MD, Herbert M.; Myers, MD, Robert P.; Sande, Jonathan R.; Barham, PhD, Steven S.; Benson, Jr. MD, Ralph C.; Dewanjee, PhD, Mrinal K.; Utz, William J., Migration and Granulomatous Reaction After Periurethral Injection of Polytef (Teflon), JAMA, Jun. 22/29, 1984: vol. 251, No. 24, pp. 3277–3281.

Bruninx, Guy; Wery, Didier; Dubois, Eric; Nakadi, Badih; Van Dueren, Eric; Verhelst, Guy; Delcour, Christian; "Emergency Endovascular Treatment of An Acute Traumatic Rupture of the Thoracic Aorta Complicated by a Distal Low–Flow Syndrome," Cardiovascular & Interventional Radiology, 22(6):515–518, Nov.–Dec. 1999.

Mitsuzaki K., Yamashita Y., Utsunomiva D., Sumi S., Ogata I., Takahashi M., Kawakami S., Ueda S., "Balloon–Occluded Retrograde Transvenous Embolization of a Pelvic Arteriovenous Malformation," Cardiovascular & Interventional Radiology 22(6):518–20, Nov.–Dec. 1999.

Dutta, Usha; Garg, Pramod K.; Agarwal, Rajeev; Gupta, S. Dutta; Prasad, G.A.; Kaul, Upendra; Tandon, Rakesh K., "Blocking of the Hepatic Vein Outflow by Neointima Covering a Wallstent Across a Membranous Stenosis of the Inferior Vena Cava", Cardiovascular & Interventional Radiology 22(6):521–523, Nov.–Dec. 1999.

Kishimoto, Keiko; Hara, Akihiko; Arita, Takeshi; Tsukamoto, Katsuhiko; Matsui, Norichika; Kaneyuke, Toshihiro; Matsunaga, Naofumi, "Stomal Varices: Treatment by Percutaneous Transhepatic Coil Embolization", Cardiovascular & Interventional Radiology 22(6):523–525, Nov.–Dec. 1999.

Shi HB., Suh DC., Lee HK., Lim SM., Kim DH., Choi CG., Lee CS., Rhim SC., "Preoperative Transarterial Embolization of Spinal Tumor: Embolization Techniques and Results," Ajnr: American Journal of Neuroradiology, 20(10):2009–15, Nov.–Dec. 1999.

EMBOLIZATION USING CARBON COATED MICROPARTICLES

BACKGROUND

Therapeutic vascular occlusions (embolizations) are techniques used to treat certain pathological conditions in situ. Therapeutic embolization is practiced generally using a catheter, under imagery control, to position particulate embolization agents in the circulatory system, such as the vessels of various processes: tumors, vascular malformations, and hemorrhagic processes. Notably, vascular occlusion can suppress pain or pressure sensations, limit blood loss (e.g., during a surgical intervention following embolization), or even prompt necrosis. In the case of vascular malformations, embolization can normalize blood flow to normal tissue, aid in surgery, and limit the risk of hemorrhage. In hemorrhagic processes, vascular occlusion produces a reduction of blood flow, which promotes cicatrization of arterial openings. U.S. Pat. No. 5,635,215 discloses the use of hydrophilic acrylic copolymer microspheres coated with a cell adhesion promoter for therapeutic embolization.

Uterine Artery Embolization (UAE) is the process of occluding the vascular blood supply to uterine fibroids to reduce fibroid size and alleviate associated symptoms, including bleeding, pain, and disfigurement. Fibroids are benign tumors of smooth muscle. They are also called leiomyomas or myomas. Fibroids may arise in different parts of the uterus. They are named by their position within the uterus; submucosal, intramural, and subserosal. Some fibroids grow on a stalk and these are called pedunculated. Abnormal bleeding can be caused by submucosal or intramural fibroids. Intramural and subserosal fibroids can cause pelvic pain, back pain, and generalized pressure sensations. Fibroids often fail to respond to medical therapies, causing either myomectomy (surgical removal of the fibroids) or hysterectomy to be an ultimate treatment.

In recent years, there has been considerable research aimed at developing less invasive alternatives to surgical treatments of fibroids. One such alternative is uterine fibroid embolization.

PCT/GB98/02621 discloses a bio-compatible, embolizing agent comprising polymer particle such as polyvinyl alcohol, containing a contrast enhancing material. The contrast enhancing materials can be located on the surface or in the pores of, or within micro-balloons formed from, the polymer particles. Consequently, the polymer particles retain a contrast enhancing effect in vivo for a prolonged period of at least seven days, or preferably at least fourteen days, and particularly preferably until the polymer particles biodegrade.

PCT/US99/04398 discloses a method for gynecological endovascular embolization with a fluid embolic composition that halicize forms a coherent solid mass. The embolization agent is a composition of biocompatible polymers and a radiopaque material. In some applications where a water soluble radiopaque material is used, the composition does not contain any particles. The particle size is no more than 100 micrometers and preferably less than 10 micrometers.

U.S. Pat. No. 4,999,188 (Solodovnik et al.) discloses a composition for embolization of blood vessels, in which agglomeration of particles is decreased as the composition is introduced. The proposed composition can additionally comprise a medicinal or radiopaque substance or a mixture of these in an amount of about 0.005 to about 8% by weight in relation to the total weight of the initial ingredients. The particles of the embolizing material may include particles of a polymer material moderately swelling in water, particles of glass or metal or a mixture thereof Suitable polymeric particles include acetylcellulose, acetylphtalylcellulose, polyvinylacetate, copolymers of vinylpyrrolidone and methylmethacrylate.

U.S. Pat. No. 5,202,352 (Okada et al.) discloses an intravascular embolizing agent containing an angiogenesis-inhibiting substance and an intravascular embolizing substance. The agent, with the administration of a relatively small dosage amount, enhances the anti-tumor effect of the angiogenesis-inhibiting substances. The addition of small doses of angiogenesis inhibiting substances also enhances the anti-tumor effect of intravascular embolizing agents.

U.S. Pat. No. 5,236,410 (Granov et al.) discloses a method for tumor treatment which involves first catheterization of the vessel that supplies a tumor of interest. A suspension of a magnetically hard ferromagnetic substance in an oil solution of oil-soluble antitumor agent is then injected through the catheter under fluoroscopic control and, at the same time, local magnetic field is applied onto the tumor-bearing area. After 1–3 days, the tumor is subjected to oscillating power field selected from ultrahigh radio frequency electromagnetic field and the field of ultrasonic contraction waves until the temperature of 43.0–43.5C is reached within the tumor, and this temperature is maintained for 5–45 minutes. In cases of large size tumors it is preferable to reduce the blood flow in the tumor-feeding blood vessel after the administration thereto of the suspension.

U.S. Pat. No. 5,624,685 (Takahashi et al.) discloses a vascular lesion embolizing material comprising a high-polymer gel capable of absorbing water in an amount of 10 ml/g and more. When the high-polymer gel is supplied, either as such or after being bound with a binder or confined in a capsule, to the site of a blood vessel having a lesion to be repaired or its neighborhood, the gel swells upon contact with blood and spreads readily in the blood vessel to close the lumen of the blood vessels with lesion.

SUMMARY OF THE INVENTION

In accordance with the present invention there is provided a method of embolization. The method includes the use of a composition that contains biocompatible particles comprising a carbon surface, preferably provided in a biocompatible carrier. The particles can preferably be radiopaque, and can preferably be in the range from about 100 microns to 1,000 microns in transverse, cross-sectional dimension. The composition can be designed to be delivered into the body through a small-bore needle, cannula, or catheter.

The carbon of the surface may be, for example, pyrolytic carbon, e.g., isotropic carbon such as low temperature isotropic carbon, vitreous carbon, or any other useful form of carbon. The carbon can be coated onto a particle substrate as a thin coating or film, thereby creating a particle that has a highly biocompatible, carbon surface. While not required, pyrolytic carbon can be preferred.

The material of the particle substrate can be but is not necessarily biocompatible, and should be capable of withstanding the conditions of the coating process, which might include elevated temperatures. In particularly preferred embodiments, particle substrates can be radiopaque most preferably permanently radiopoque. Exemplary materials for radiopaque particle substrates can include metals and metal oxides such as zirconium oxide and aluminum oxide. Carbon itself, such as graphite or low temperature isotropic carbon, or other forms of carbon, may also be used as the particle substrate as well as other materials such as ceramics.

The fluid carrier can preferably be any biologically compatible material capable of delivering microparticles to a desired location, such as a biologically compatible suspension, solution, or other form of a fluid or gel. Specific examples of materials useful in biologically compatible carriers include saline, dextrans, glycerol, polyethylene glycol, and other polysaccharides or biocompatible polymers, either singly or in combination.

The use of the carbon-coated microparticles described herein has advantages over the use of other microparticles. Microparticles comprising a carbon coating, e.g., pyrolytic carbon, are very biocompatible. Preferred embodiments of the microparticle can be permanently radiopaque, e.g., by virtue of a radiopaque particle substrate. The location of the radiopaque particles can be monitored, by known methods, for as long as the radiopaque microparticles remain in a body. This is an improvement over many prior art contrastenhancing agents which biodegrade or otherwise lose their radiopacity over a period of days or weeks.

An aspect of the invention relates to a method for embolization including delivery of an embolic agent composition to a blood vessel to fill or plug the blood vessel and/or encourage clot formation so that blood flow through the vessel is reduced or stopped. The embolic agent composition contains microparticles having a carbon surface. The carbon can preferably be pyrolytic carbon. The microparticles can preferably contain a contrasting agent, and are most preferably radiopaque by virtue of a permanently radiopaque particle substrate.

Another aspect of the invention relates to a method for gynecological embolization. The method includes delivering an embolic agent composition to a blood vessel, the embolic agent composition including microparticles comprising a carbon surface. The carbon can preferably be pyrolytic carbon. The microparticles can preferably contain a contrasting agent, and are most preferably radiopaque by virtue of a permanently radiopaque particle substrate.

For purposes of the present disclosure, the following terms shall be given the following meanings.

The term "biocompatible," refers to materials which, in the amount employed, are non-toxic and substantially nonimmunogenic when used internally in a patient, and which are substantially insoluble in blood. Suitable biocompatible materials include ceramics, metals such as titanium, gold, silver, stainless steel, metal oxides, carbon such as pyrolytic carbon or ultra low temperature isotropic carbon, etc.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

DETAILED DESCRIPTION

Embolization is a process wherein a material is injected into a blood vessel to at least partially fill or plug the blood vessel and/or encourage clot formation so that blood flow through the vessel is reduced or stopped (see background, supra). Embolization of a blood vessel can be useful for a variety of medical reasons, including preventing or controlling bleeding due to lesions (e.g., organ bleeding, gastrointestinal bleeding, vascular bleeding, and bleeding associated with an aneurysm), or to ablate diseased tissue (e.g., tumors, vascular malformations, hemorragic processes, etc.) by cutting off blood supply. Embolization may also be used to prevent blood loss during or immediately following surgery. Embolization of tumors may be performed preoperatively to shrink tumor size and to aid in visualization of a tumor and to prevent blood loss related to surgical procedures.

Emobilization may be used in treating skin, head, or neck tumors, tumors of the uterus or fallopian tubes, liver or kidney tumors, endometriosis, fibroids, etc. Particularly, embolization has been used for arteriovenous malformation of the pelvis, kidney, liver, spine and brain. Uterine artery embolization has been used for the treatment of fibroids; renal artery embolization has been used for the treatment of renal angiomyolipomas and renal cell carcinoma; intracranial embolization has been used for the treatment of cerebral and intracranial aneurysms, neuroendocrine metastases, intracranial dural arteriovenous fistula and patent ductus arteriosus. Other examples of specific procedures include hepatic artery ebmolization and pulmonary artery embolization. Examples of such procedures are described, e.g., in Mourikis D., Chatziioannou A., Antoniou A., Kehagias D., Gikas D., Vlahous L., "Selective Arterial Embolization in the Management of Symptomatic Renal Angiomyolipomas (AMLs)," European Journal of Radiology 32(3):153–9, 1999 Dec.; Kalman D. Varenhorst E., "The Role of Atrerial Embolization in Renal Cell Carcinoma," Scandinavian Journal of Urology & Nephrology, 33(3):162–70, 1999 Jun.; Lee W., Kim T S., Chung J W., Han J K., Kim S H., Park J H., "Renal Angiomyolipoma: Embolotherapy with a Mixture of Alcohol and Iodized Oil," Journal of Vascular & Interventional Radiology, 9(2):255–61, 1998 March-April; Layelle I., Flandroy P., Trotteur G., Dondelinger R F., "Arterial Embolization of Bone Metastases: is it Worthwhile?" Journal Belge de Radiologie, 81(5):223–5, 1998 Oct.; Berman, M F., Hartmann A., Mast H., Sciacca R R., Mohr J P., PileSpellman J., Young W L., "Determinants of Resource Utilization in the Treatment of Brain Arteriovenous Malformations," Ajnr: American Journal of Neuroradiology, 20(10):2004–8, 1999 Nov.–Dec.; Shi H B., Suh D C., Lee H K., Lim S M., Kim D H., Choi C G., Lee C S., Rhim S C., "Preoperative Transarterial Embolization of Spinal Tumor: Embolization Techniques and Results," Ajnr: American Journal of Neuroradiology, 20(10):2009–15, 1999 Nov–Dec.; Nagino M., Kamiya J., Kanai M., Uesaka K., Sano T., Yamamoto H., Hayakawa N., Nimura Y., "Right Trisegment Portal Vein Embolization for Biliary Tract Carcinoma: Technique and Clinical Utility," Surgery, 127(2) :155–60, 2000 Feb.; Mitsuzaki K., Yamashita Y., Utsunomiva D., Sumi S., Ogata I., Takahashi M., Kawakami S., Ueda S., "Balloon-Occluded Retrograde Transvenous Embolization of a Pelvic Arteriovenous Malformation," Cardiovascular & Interventional Radiology 22(6):518–20, 1999 Nov–Dec.

While portions of the present description include language relating specifically to gynecological embolization, all types of embolization processes are considered to be within the contemplation of the present invention. Specifically, one of skill in the medical or embolizing art will understand and appreciate how carbon-coated microparticles as described herein can be used in various embolization processes by guiding a delivery mechanism to a desired vascular body site, and delivering of an amount of the microparticles to the site, to cause restriction, occlusion, filling, or plugging of one or more desired vessels and reduction or stoppage of blood flow through the vessels. Factors that might be considered, controlled, or adjusted for, in applying the process to any particular embolization process might include the chosen composition of the microparticles (e.g., to account for imaging, tracking, and detection of a radiopaque particle substrate); the amount of microparticles delivered to the body site; the method of delivery, including the particular equipment (e.g., catheter) used and the method and route used to place the dispensing end of the catheter at the desired body site, etc. All of these factors will be appreciated by one of ordinary skill, and can be readily dealt with to apply the described methods to a large variety of embolization processes.

Embolization typically is performed using angiographic techniques and with guidance and monitoring, e.g., fluoroscopic or X-ray guidance, to deliver an embolizing agent to vessels or arteries. A vasodilator (for example adenosine) may be administered to the patient beforehand, simultaneously, or subsequently, to the procedure to facilitate the procedure.

Gynecological embolization refers to embolization used to control acute and chronic genital bleeding in an obstetric or gynecological disorder, including uterine fibroids. Uterine Arterial Embolization (UAE) is a method of treating fibroids involving occluding uterine arteries that supply blood to the fibroid. Cutting off the blood supply reduces the size of the fibroid and alleviates symptoms such as bleeding, pain, and disfigurement.

At least two general variations of UAE are known. A first method, known generally as intravascular embolizaton, introduces a catheter through an artery, e.g., the femoral artery, and guides the catheter to a uterine artery. The second type of method introduces a catheter trancervically and guides the catheter into or through the uterine wall to directly access blood vessels to be embolized. The second method is considered to be less invasive and, accordingly, better tolerated as compared to intravascular methods.

Embolization procedures can typically include the following steps. A patient is sedated so as to be very sleepy during the procedure. For intravascular gynecological embolization, the uterine arteries can be accessed from the femoral artery, which is at the crease at the top of the leg. A needle can be used to puncture and enter the artery to provide access for a catheter. Local anesthesia can be used for this portion of the procedure. The catheter is advanced over the branch of the aorta and into the uterine artery on the side opposite the puncture, to a point where the artery divides into multiple vessels supplying blood to the uterus and uterine fibroids. The catheter can be steered through the artery by known techniques, e.g., using X-ray imaging, to guide the catheter's progress. The procedure can be performed on both sides of the uterus so the blood supply is blocked in both the right and left uterine arteries. Some physicians block both uterine arteries from a single puncture site, while others puncture the femoral artery at the top of both legs, in which case a second arterial catheter is placed from the opposite femoral artery to the other uterine artery. Before starting delivery of the embolizing agent composition, an arteriogram is performed to provide a road map of the blood supply to the uterus and fibroids.

In a transcervical method, a catheter capable of penetrating a vessel to be embolized, such as a needle tipped catheter, is inserted through the cervix into the uterus using a device such as a hysteroscope, allowing visualization of the uterine wall. Generally, the patient is prepared in the usual manner for a hysteroscopic procedure, and a warm saline solution is infused to inflate the uterus and help visualize the uterine wall using the hysteroscope. Then the catheter is inserted through the scope. The vessel to be embolized is located and the catheter is inserted into or through the uterine wall and into the located vessel, e.g., the position of a uterine fibroid is determined and the needle tip of the catheter is placed in a blood vessel feeding or within the fibroid mass. Repeated placement of the catheter may be needed to completely embolize the vasculature of a uterine fibroid. Such a method is described, e.g., in International Publication Number WO 99/43366, incorporated herein by reference.

The catheter delivering the embolizing agent composition may be a small diameter medical catheter. The particular catheter employed is not critical, provided that catheter components are compatible with the embolizing agent composition (i.e., the catheter components will not readily degrade in the embolizing agent composition, and vice versa). In this regard, polyethylene catheter components can be generally useful. Other materials compatible with the embolizing agent composition may include fluoropolymers (e.g., Teflon™), silicone, etc.

Once a catheter is in place, an embolizing agent composition containing microparticles is injected through the catheter slowly, typically with the assistance of X-ray or flouroscopic guidance. The microparticles are of a size that will effectively wedge in the vessels leading to the fibroids, occluding the vessel and reducing or preventing the flow of blood to the fibroid. The particles should also be of sufficient size that they do not remain mobile in the body. If the particles are too small, they can be engulfed by the body's white cells (phagocytes) and carried to distant organs or be carried away in the microvasculature and travel until they reach a site of greater constriction. For the method of the present invention, preferred particles can have a transverse cross-sectional dimension between 100 and 1,000 micrometers.

The embolizing agent composition can be introduced directly into critical blood vessels (e.g., in the transcervical procedure), or they may be introduced upstream of target vessels (especially in an intravascular procedure). If introduced upstream from a target vessel, e.g., in fibroid embodization, the microparticles flow to the fibroids first, because the fibroids are very vascular. Over several minutes, the arteries are slowly blocked. The embolization is continued until there is nearly complete blockage of blood flow in the vessel.

The amount of embolizing agent composition, and microparticles, introduced during an embolization procedure can be an amount sufficient to cause embolization, e.g., to reduce or stop blood flow through the target vessels. The amount of embolizing agent composition delivered can vary depending on the total of the vasculature to be embolized, the concentration and size of the microparticles, etc. Such factors are within the skill of the an artisan in the embolizing art.

After embolization, another arteriogram can be performed to confirm the completion of the procedure. Arterial flow will still be present to some extent to healthy body tissue proximal to the embolization, e.g., to normal portions of a uterus, while flow to the diseased or targeted tissue, e.g., fibroid is blocked. The procedure can take approximately 1 to 1 ½ hours. As a result of the restricted blood flow, the diseased or targeted tissue, e.g., tumor (or tumors), begins to shrink.

According to the invention, the embolizing agent composition comprises an injectable combination of microparticles in a biocompatible carrier.

The microparticles have a surface that comprises carbon. The carbon-containing particle surface may be in the form of a carbon-containing coating or carbon-containing film, e.g., isotropic carbon, pyrolytic carbon, or vitreous carbon, preferably in a form that is biocompatible. Various forms of carbon are described, e.g., in the article "Material Properties and Applications of Pyrolite ® Carbon," by Al Beavan, as published in *Materials Engineering*, February 1990, incorporated herein by reference. Examples of carbon coated particles are described, e.g., in U.S. Pat. No. 5,792,478, incorporated herein by reference.

The atomic structure of both pyrolytic, e.g., LTI carbon, and vitreous carbon is similar to graphite, the common form of carbon, but the alignment between hexagonal planes of atoms is not as well ordered. Pyrolytic carbon is characterized by a more chaotic atomic structure with warped hexagonal planes, missing atoms, and generally a more turbostatic appearance. This results in better bonding between layer planes. See Beavan.

The microparticles can preferably be constructed as a particle substrate having a carbon surface, e.g., a particle substrate having a layer of carbon coated thereon. While the substrate need not be biocompatible due to its being coated with a preferably biocompatible layer comprising carbon, it can be preferred that the particle substrate also be biocompatible.

The embolizing agent composition can preferably comprise a contrast-enhancing agent which can be tracked and monitored by known methods, including radiography or fluoroscopy. The contrast-enhancing agent can be any material capable of enhancing contrast in a desired imaging modality (e.g. magnetic resonance, X-ray (e.g. CT), ultrasound, magnetotomography, electrical impedance imaging, light imaging (e.g. confocal microscopy and fluorescence imaging) and nuclear imaging (e.g. scintigraphy, SPECT and PET)), and is preferably capable of being substantially immobilized within the particles, e.g., included in the microparticles as part of a carbon coating or as part of a particle substrate. Contrastenhancing agents are well known in the arts of embolization and similar medical practices, with any of a variety of such contrast-enhancing agents being suitable for use according to the methods of the invention.

Preferred embodiments of the invention can include a contrast-enhancing agent that is radiopaque in nature, in particular, a radiopaque material which exhibits permanent radiopacity, as many metals or metal oxides do. Permanent radiopacity is unlike some other contrast-enhancing agents or radiopaque materials used in embolization or similar medical applications which biodegrade or otherwise lose their effectiveness (radiopacity) over a certain period, e.g., days or weeks, such as 7 to 14 days. (See, e.g., PCT/GB98/02621). Advantage is that permanent radiopaque materials can be monitored or tracked for as long as they remain in the body, whereas other non-permanent contrast-enhancing agents or radiopaque materials have a limited time during which they may be detected and tracked.

The contrast-enhancing agent may be incorporated into the microparticle as part of the particle substrate, as part of the carbon surface, or elsewhere. In one sense, a contrastenhancing agent can be added to a material that is not detectable, e.g., not radiopaque, to make that material detectable. The contrast-enhancing agent may be provided in any such portion of a microparticle by known methods. According to a preferred mode of the invention, a permanent radiopaque material such as a metal or metal oxide can act as the particle substrate upon which a non-radiopaque carbon coating is placed. The particle substrates themselves are permanently radiopaque, and can be individually and permanently detected and tracked following deposition into the body.

Some examples of radiopaque materials include paramagnetic materials (e.g. persistent free radicals or more preferably compounds, salts, and complexes of paramagnetic metal species, for example transition metal or lanthanide ions); heavy atom (i.e. atomic number of 37 or more) compounds, salts, or complexes (e.g. heavy metal compounds, iodinated compounds, etc.); radionuclide-containing compounds, salts, or complexes (e.g. salts, compounds or complexes of radioactive metal isotopes or radiodinated organic compounds); and superparamagentic particles (e.g. metal oxide or mixed oxide particles, particularly iron oxides). Preferred paramagnetic metals include Gd (III), Dy (III), Fe (II), Fe (III), Mn (III) and Ho (III), and paramagnetic Ni, Co and Eu species. Preferred heavy metals include Pb, Ba, Ag, Au, W, Cu, Bi and lanthanides such as Gd, etc.

The amount of contrast-enhancing agent included in a microparticle should be sufficient to allow detection of the microparticle as desired. Preferably, microparticles of the embolizing agent composition can comprise from about 10 to about 50 weight percent of contrast-enhancing agent, more preferably from about 20 to 40 weight percent contrastenhancing agent, and even more preferably about 30 weight percent contrast-enhancing agent. Optionally, some, i.e., only a portion, but not all microparticles used in a particular embolization procedure can include a contrast-enhancing agent. Microparticles that include a permanent radiopaque particle substrate can preferably have greater than 50 percent of their mass made up of the particle substrate.

The microparticles may be prepared using any of a variety of coating processes to deposit carbon onto a particle substrate. The particle substrate can be selected for compatibility with the coating process, meaning that it should be capable of withstanding temperatures used in a given process for coating carbon onto a particle substrate. Relatively hard metallic or ceramic materials capable of withstanding high temperature conditions of a coating process can generally be preferred materials for the particle substrate. Metals, metal oxides, and alloys, including but not limited to medical grade stainless steel, titanium and titanium alloys, and oxide derivatives of stainless steel or titanium or titanium alloys, are also quite acceptable materials for the particle substrate, with aluminum oxide, and zirconium oxide being especially suitable. Carbon itself in any of its various forms, e.g., pyrolytic carbon, non-pyrolytic carbon, isotropic carbon, graphite, or vitreous carbon, may be useful as a particle substrate material. Thus, the microparticles may include a carbon coating deposited on a carbon particle substrate, and may be substantially or entirely made of carbon. In one embodiment of the invention, both the particle substrate and the carbon coating may comprise pyrolytic carbon.

The particle substrates, whatever their composition, should be of sufficient diameter, shape, and uniformity that they can be coated with carbon, as described, to produce carboncoated particles of a size, quality, and nature as described herein. Optionally, the particle substrates, prior to coating, can be selected and processed, e.g., milled, extruded, sifted, cleaned, filtered, or otherwise formed, etc., to provide a desired combination of particle size, shape, and quality, to result in coated particles of a desired size, shape, and quality.

The carbon surface of the microparticles may comprise any form of carbon, with pyrolytic carbon, especially low temperature isotropic (LTI) pyrolytic carbon, being one preferred form. Pyrolytic carbon can be produced and coated onto a substrate surface by known methods, e.g., as described in the Beavan article, and in U.S. Pat. No. 5,792,478, cited above. Generally, hydrocarbons and alloying gases are decomposed to prepare a pyrolytic carbon coating on a particle substrate. The particle substrates are included with the hydrocarbons and alloying gases in a fluidized or floating bed at a temperature sufficient to cause deposition of pyrolyzed carbon onto the substrate surface, e.g., from about 1200 to 1500F (see Beavan, p.2). Inert gas flow is used to float the bed of particle substrates, optionally including an inert mixing media. The hydrocarbon pyrolysis results in a high carbon, low hydrogen content carbon material being deposited as a solid material on particle substrates.

Alternatively, a carbon coating (sometimes referred to as "ultra-low-temperature isotropic carbon") may be applied to a particle substrate using other coating processes, e.g., a vacuum vapor deposition process. Such a coating can be effectively produced and deposited onto a particle substrate using ion beams generated from any of a variety of known processes, such as the disassociation of $CO_2$, reactive dissociation in vacuum of a hydrocarbon as a result of a glow discharge, sublimation of a solid graphite source, or cathode sputtering of a graphite source. Gold has been found to be an especially suitable substrate material ideal for vacuum vapor deposited carbon. Other substrates, including but not limited to nickel, silver, stainless steel, or titanium are also quite acceptable as a substrate material for the type of coating process.

The coating process is applied to substrate particles to produce final, preferably generally rounded particles that have a smooth carbon-coated surface in the form of a thin coating or film. The resulting smooth surface enhances passage of the microparticles through an injection needle, cannula, or catheter. The high strength, resistance to breakdown or corrosion, and durability of the carbon surface ensures effective, long term functioning of the particles. The established biocompatibility of carbons such as pyrolytic and vitreous carbon makes the described particles particularly suitable for the embolization applications. In a preferred embodiment of carbon-coated microparticles, the particle substrates have been completely encased by a carbon surface. This results in a smooth coated particle with no substrate exposure on the surface of the particle or in contact with tissue when injected. Preferred carbon coatings can be in the range of fractions of thousandths of an inch, e.g., about one half of a thousands of an inch (0.0005 inches), on average, covering the surface of the particle substrate.

After the carbon coating has been deposited onto the particle substrate, the microparticles are subjected to a cleaning and sieving process to remove contaminants and to separate out particles of a size less than or greater than a desired size range. The particles may preferably range in size from 100 microns to 1,000 microns in average, transverse cross-sectional dimension, and a particularly preferred size range can be between 400 and 700 microns. The particles may be processed, e.g., segregated to a selected size range, for example using a sieving process such that the minimum microparticle dimension will pass through a U.S. No. 18 Screen Mesh (1000 micron grid size opening) but will not pass through a U.S. No. 140 Screen Mesh (106 micron grid size). That minimum dimension will be the transverse, cross-sectional dimension on oblong or elongated particles, with that dimension coinciding with the particle diameter on generally spherical particles.

As stated, the carrier can be any biocompatible fluid capable of delivering the microparticles to a desired site. Examples of suitable materials for a carrier can include saline, dextran, glycerol, polyethylene glycol, corn oil or safflower, or other polysaccharides or biocompatible organic polymers either singly or in combination. In use, the embolic agent composition can typically be injected in a fluid state, e.g., as a slurry, fluid suspension or emulsion, or as a gel, through a catheter, syringe needle, or cannula into a body site. When deposited into the blood stream, the carrier will disperse or be destroyed.

What is claimed is:

1. A method for embolization comprising delivering an embolic agent composition to a blood vessel to fill or plug the blood vessel and/or encourage clot formation so that blood flow through the vessel is reduced or ceases, the embolic agent composition comprising microparticles comprising a carbon surface.

2. The method of claim 1 wherein the carbon comprises pyrolytic carbon.

3. The method of claim 1 wherein the carbon comprises low temperature isotropic pyrolytic carbon.

4. The method of claim 1 wherein the average, transverse cross-sectional dimension of the microparticles is between 100 and 1,000 micrometers.

5. The method of claim 1 wherein the microparticles comprise a carbon-coated substrate particle and the substrate particle comprises a metal, a metal oxide, a ceramic, carbon, or a combination thereof.

6. The method of claim 1 wherein the microparticles comprise a radiopaque substrate particle having a carbon surface.

7. The method of claim 6 wherein the radiopaque substrate is permanently radiopaque.

8. The method of claim 7 wherein the substrate comprises a metal or a metal oxide.

9. The method of claim 8 wherein the substrate comprises aluminum oxide, zirconium oxide, or a mixture thereof.

10. The method of claim 1 wherein the embolic agent composition further comprises a biocompatible carrier to carry and deliver the microparticles.

11. The method of claim 1 wherein the method comprises embolizing a renal artery.

12. The method of claim 1 wherein the method comprises embolizing a hepatic artery.

13. The method of claim 1 wherein the method comprises embolizing a pulmonary artery.

14. The method of claim 1 wherein the method comprises intracranial embolization.

15. The method of claim 14 wherein the method comprises embolization of an intracranial aneurysm, a cerebral aneurysm, neuroendocrine metastases, intracranial dural arteriovenous fistula, or patent ductus arteriosus.

16. The method of claim 1 wherein the method comprises embolizing a uterine artery to treat a uterine fibroid.

17. The method of claim 16 wherein the method comprises injecting the embolic agent composition into a uterine artery.

18. The method of claim 17 comprising introducing a catheter through a femoral artery and inserting the catheter into a blood vessel which feeds or is within a fibroid mass.

19. The method of claim 17 comprising introducing the catheter transcervically, and inserting the catheter through the uterine wall and into a blood vessel which feeds or is within a fibroid mass.

20. The method of claim 1 comprising the step of detecting the microparticle after delivery to confirm placement at the designated site.

21. A method for gynecological embolization comprising delivering an embolic agent composition to a blood vessel, the embolic agent composition comprising microparticles comprising a carbon surface.

22. The method of claim 21 wherein the microparticles are radiopaque.

23. The method of claim 21 wherein the microparticle surface comprises pyrolytic carbon.

24. The method of claim 21 wherein the embolic agent composition further comprises a biocompatible carrier to carry and deliver the microparticles.

25. The method of claim 21 wherein the blood vessel is proximal to a uterine fibroid.

26. The method of claim 21 comprising inserting a catheter through the femoral artery, guiding the catheter to a uterine artery, and delivering the embolic agent composition to a blood vessel proximal to a uterine fibroid.

27. The method of claim 21 comprising inserting a catheter capable of penetrating a blood vessel through a cervix, guiding the catheter to a uterine blood vessel proximal to a uterine fibroid, and delivering the embolic agent composition to the uterine blood vessel.

28. The method of claim 21 comprising the step of detecting the microparticle after delivery to confirm placement at the designated site.

* * * * *